United States Patent [19]

Birum

[11] 4,073,767
[45] Feb. 14, 1978

[54] HYDROGEN PHOSPHONATES AND POLYMERS CONTAINING THEM AS FLAME RETARDANTS

[75] Inventor: Gail H. Birum, Kirkwood, Mo.
[73] Assignee: Monsanto Company, St. Louis, Mo.
[21] Appl. No.: 720,487
[22] Filed: Sept. 3, 1976
[51] Int. Cl.$^2$ .......................... C07F 9/08; C08K 5/53
[52] U.S. Cl. .......................... 260/45.8 R; 260/927 R; 260/937
[58] Field of Search ............... 260/45.8 R, 927 R, 937

[56] References Cited

U.S. PATENT DOCUMENTS

| | | | |
|---|---|---|---|
| 2,957,856 | 10/1960 | Guest et al. | 526/225 |
| 3,413,382 | 11/1968 | Ulrich | 260/937 |
| 3,887,655 | 6/1975 | Shim | 260/937 |
| 3,966,849 | 6/1976 | Noetzel et al. | 260/45.8 R |
| 3,978,167 | 8/1976 | Albright | 260/927 R |
| 3,997,505 | 12/1976 | Albright | 260/45.8 R |
| 4,007,236 | 2/1977 | Duffy et al. | 260/927 R |

OTHER PUBLICATIONS

Sebring — Chem. Abs. 79, 115722k (1973).

*Primary Examiner*—Donald E. Czaja
*Assistant Examiner*—H. H. Fletcher
*Attorney, Agent, or Firm*—Herman O. Bauermeister

[57] ABSTRACT

The present invention relates to cyclic phosphorus compounds and processes for the preparation thereof.

The present invention relates to a process for the preparation of certain derivatives of cyclic hydrogenphosphonates. Azomethine, sulfonyl isocyanate, isocyanate, and isothiocyanate derivatives are a part of the present invention.

The cyclic phosphorus compounds are useful as flame retardants with organic polymers, such as polyurethanes, polyesters, and polyamides.

17 Claims, No Drawings

HYDROGEN PHOSPHONATES AND POLYMERS CONTAINING THEM AS FLAME RETARDANTS

BACKGROUND OF THE INVENTION

The present invention relates to cyclic phosphorus compounds, such as certain cyclic hydrogen phosphonate derivative, processes for the preparation of such compounds and their derivatives and to flame retardant compositions containing the said cyclic phosphorus compounds.

Certain phosphonates have been employed as flame retardant additives, but have suffered from the defect of causing undesirable crosslinking of polymeric materials in which the phosphonates were employed. For example, the addition of such phosphonates to a molten polymer such as polyethylene terephthalate or a nylon, preliminary to the extrusion or spinning step has shown that the crosslinking prevents the formation of acceptable fibers. As a result of the crosslinking, the fibers contain lumps and irregular sections so that the extrusion through spinnerettes is hampered and the stretching, washing and other physical treatments of the fiber become impossible.

It has now however been found that certain cyclic phosphorus compounds including cyclic phosphonates are particularly useful as flame retardants for organic polymeric materials. The invention includes combinations of the present cyclic phosphorus compounds together with organic polymers such as polyurethanes, polyesters, e.g. polyethylene terephthalate, and polyamides e.g., the nylons.

SUMMARY OF THE INVENTION

The general formula for the cyclic phosphorus derivatives of the invention is:

where Y is selected from the group consisting of

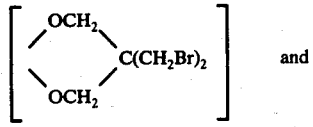 and

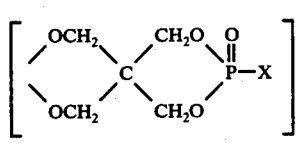

and where X is selected from the group consisting of

| | |
|---|---|
| 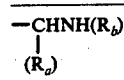 | where $R_a$ is an alkyl radical of 1 to 4 carbon atoms, $R_b$ is a phenyl radical of 6 to 10 carbon atoms. |
|  | where $R_c$ is phenyl with 0 to 2 halogens or phenyl with 0 to 2 nitro groups or phenyl with 0 to 2 methyl groups. |
|  | where $R_d$ is phenyl with 0 to 2 halogen atoms, or phenyl with 0 to 2 methyl groups, or an alkyl or alkenyl radical of 1 to 3 carbon atoms. |
|  | where $R_e$ is phenyl with 0 to 2 halogens, or alkyl or alkenyl of 1 to 3 carbon atoms. |

The above compounds are derivatives of cyclic hydrogenphosphonates. They are obtained by the reaction of a crude or purified hydrogen phosphonate with azomethines, sulfonyl isocyanates, isocyanates and isothiocyanates respectively.

Representative examples of azomethines are N-(p-chlorobenzylidene) ethylamine, and N,N'-terephthalylidene-di-p-toluidine, and benzylidene ethylamine, and p-chlorobenzylidenemethylamine, and methyl benzylidenemethylamine.

The general reaction for the preparation of the azomethine derivatives is:

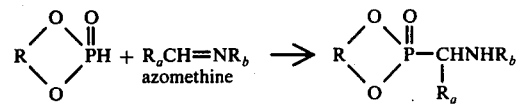

Examples of isocyanates that can be used are: p-toluenesulfonylisocyanate, methyl sulfonylisocyanate, ethyl sulfonylisocyanate, phenylsulfonylisocyanate, chlorophenylsulfonylisocyanate, p-nitrophenylsulfonylisocyanate, p-nitrophenyl isocyanate, allyl isocyanate, p-chlorophenylisocyanate, 2-fluorophenylisocyanate, α,α,α-trifluoro-m-tolyl isocyanate, methyl isocyanate, 3-bromophenyl isocyanate, tolylene-2,4-diisocyanate, and 1,6-diisocyanatehexane. Examples of isothiocyanates that can be used are: allylisothiocyanate, ethyl isothiocyanate, 4-fluorophenyl isothiocyanate, 2-naphthyl isothiocyanate, methyl isothiocyanate, and 4-chloro-2-naphthyl isothiocyanate.

The general reactions for the preparation of the sulfonyl isocyanate derivatives, isocyanate derivatives and isothiocyanates are shown below:

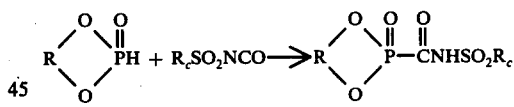

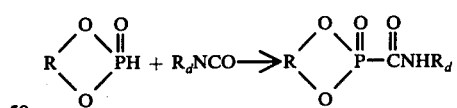

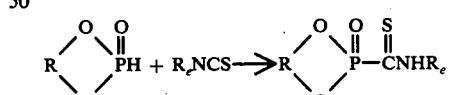

Where R is an alkylene, or haloalkylene (halo is chlorine or bromine), group of a 1,2-glycol having from 2 to 8 carbon atoms, or of a 1,3 glycol having from 3 to 8 carbon atoms.

The present cyclic phosphorus compounds of the invention including hydrogen phosphonates, are useful per se as flame retardant materials which provide phosphorus as a component to reduce flammability. Improvement in flame retardant properties result when the present derivatives are used with organic polymers. Such resultant products do not burn readily, and instead inhibit flammability of an organic polymer, for instance a polyurethane which is useful in the production of an elastomer or a rigid or flexible foam. An example of an elastomeric polyurethane is the product obtained by heating together poly(tetramethylene ether)glycol and methylene bis(p-phenylisocyanate).

The cyclic phosphorus compounds including the cyclic hydrogen phosphonates of the present invention are useful as flame retardant modifiers for organic polymers. The cyclic phosphorus compounds have less tendency to cause cross linking. These compounds can be added directly to the molten polymer or the components of a foam composition before polymerization, e.g. before spinning fibers or forming films or other shaped objects including foamed plastics. Typical polymers are polyesters, polyamides, polyurethanes, polyolefins, nitrile polymers such as polyacrylonitrile, vinyl polymers such as vinyl chloride, styrene polymers and copolymers such as acrylonitrile-butadienestyrene compositions.

The general reaction of the process for the production of hydrogen phosphonates is based upon the use of formic acid with a phosphorohalidite, such as a phosphorochloridite, represented in the process below by the structure,

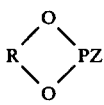

where R is an alkylene, or haloalkylene group of a 1,2-glycol having from 2 to 8 carbon atoms, or of a 1,3 glycol having from 3 to 8 carbon atoms, and Z is Cl or Br. An example is:

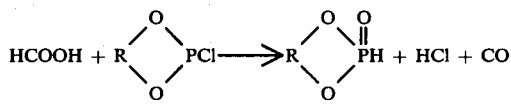

Examples of specific useful phosphorochloridites are the bis(phosphorochloridites), such as 3,9-dichloro-2,4,8,10-tetraoxa-3,9-diphosphaspiro[5.5]undecane,

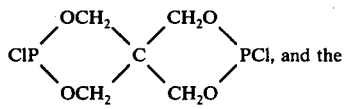

corresponding bromo derivative; 2-chloro-5,5-bis(bromomethyl)-1,3,2-dioxaphosphorinane,

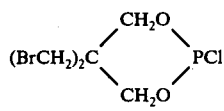

and the related phosphorochloridites, 2-chloro-5,5-dimethyl-1,3,2-dioxaphosphorinane, and 2-chloro-5-ethyl-5-methyl-1,3,2-dioxaphosphorinane, and 2-bromo-5,5-bis(chloromethyl)-1,3,2-dioxaphosphorinane, and 2-chloro-5-phenyl-1,3,2-dioxaphosphorinane, and 2-chloro-5-(4-fluoro-3-bromophenyl)-1,3,2-dioxaphosphorinane.

The process of converting cyclic phosphorochloridites to cyclic hydrogen phosphonates can also be applied to five-membered ring phosphorochloridites, e.g., 4,5-dimethyl-2-chloro-1,3,2-dioxaphospholane, 2-chloro-1,3,2-dioxaphospholane, 2 butyl-1,3,2-dioxaphospholane, 4-chloromethyl-1,3,2-dioxaphospholane, and 4-methyl-1,3,2-dioxaphospholane.

The method of treating cyclic phosphorochloridites with formic acid provides an improved process for producing cyclic hydrogenphosphonates, sometimes called cyclic phosphites. Some earlier workers in this area of phosphorus chemistry have also called these compounds cyclic hydrogen phosphites, but preferable general terminology is to call these compounds cyclic hydrogenphosphonates because it better describes the predominant pentavalent state of the phosphorus. A number of methods are known for preparing cyclic hydrogenphosphonates, such as the use of triethylamine as an acid-binding agent in the hydrolysis of cyclic chlorophosphites (cyclic phosphorochloridites). In this procedure, an amine hydrochloride is produced as a by-product, and this must then be separated from the desired cyclic hydrogenphosphonate.

In the above process, using formic acid instead of water, the by-products are anhydrous hydrogen chloride and carbon monoxide, gaseous products which are easily removed, leaving easily isolated cyclic hydrogenphosphonate. For example, when attempts were made to prepare 3,9-H-3,9-dioxo-2,4,8,10-tetraoxa-3,9-diphosphaspiro[5.5]undecane(I),

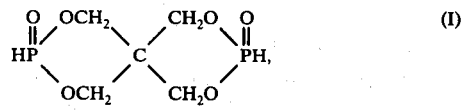

by treatment of 3,9-dichloro-2,4,8,10-tetraoxa-3,9-diphosphospiro[5.5]undecane with water by the prior art procedures, none of the desired product could be isolated from the mixture of side reaction products. However, when formic acid is used according to the present invention, essentially pure and easily isolated compound I is obtained.

Catalysts are unnecessary in the above process for preparing hydrogen phosphonates. A solvent is generally unnecessary when formic acid is used for conversion of cyclic phosphorochloridites to cyclic hydrogenphosphonates. Inert solvents or suspending liquids, e.g. acetonitrile, benzene and 1,2-dichloroethane, can however be used to aid mixing and temperature control.

The reaction is usually carried out by the addition of formic acid to the stirred phosphorochloridite at 10° to 100° C, preferably 30° to 70° C, while allowing the by-products hydrogen chloride (or hydrogen bromide) and carbon monoxide to be expelled through a condenser and then trapped or absorbed by suitable and safe methods such as neutralization. In one case, this mixture of gases is passed into a stirred suspension of aluminum trichloride and toluene to produce p-tolualdehyde by the Gatterman-Koch Reaction, thus confirming the composition of the effluent gases and demonstrating a practical by-product recovery application.

The process for the preparation of the said derivatives or adducts, e.g., the azomethine, sulfonyl isocyanate, isocyanate or isothiocyanate derivatives, is carried out at 0° to 100° C. No solvent is necessary, although inert solvents such as benzene, toluene and chlorobenzene may be used.

For the process, a basic catalyst is desirable. Examples of presently useful basic catalysts are, e.g. the heterocyclic nitrogen bases such as N-methylmorpholine, pyridine, quinoline, N-ethylpiperidine, picoline, quinaldine, 4-methylpyrinidine, or N-phenylpyrazole; the tertiary amines such as triethylamine, trimethylamine, tri-tert-butylamine, N,N-dimethylaniline, N-benzyl-N-methylaniline, and alkylene polyamines such as triethylenediamine; quaternary ammonium compounds such as benzyltrimethylammonium methoxide or tetrabutylammonium butoxide; alkali metal alkoxides such as sodium or potassium methoxide or propoxide, etc. The quantity of catalyst to be used will depend upon the nature of the azomethine isocyanate, and cyclic hydrogenphosphonate, obviously the more reactive reactants will require less catalyst than will the somewhat more sluggish reaction components. Whether or not a diluent is used will likewise regulate catalyst quantity. Also variable is the temperature at which reaction is effected; for, here again must be taken into consideration the nature of the reactants, catalyst quantity, and whether or not a diluent is used. The reaction is generally exothermic; hence the present addition reactions can be conducted at ordinary room temperature or even at decreased temperatures, but heating of the reaction mixture may be needed to complete the reaction. All of these variables, i.e. catalyst quantity, use of diluent and temperature conditions can readily be arrived at by easy experimentation.

The cyclic hydrogenphosphonates and azomethines react according to the following equation to produce products of the present invention.

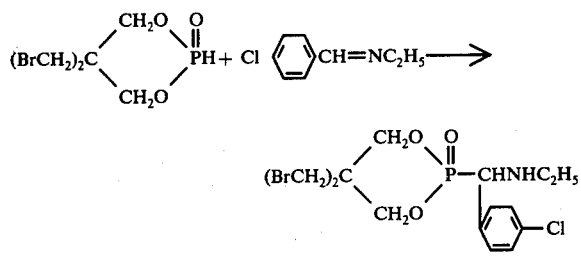

An example of the reaction of sulfonylisocyanates with cyclic hydrogenphosphonates is illustrated by the following equation.

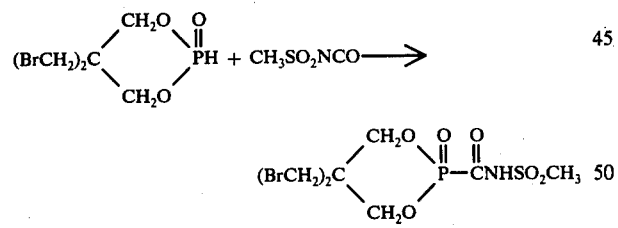

Isothiocyanates and cyclic hydrogenphosphonates react similarly as represented in the following equation.

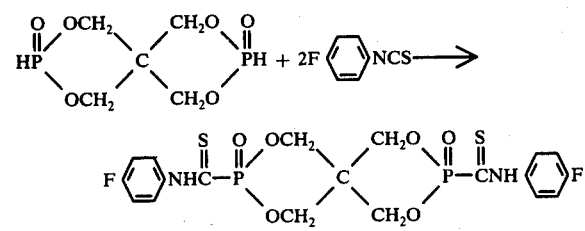

The compounds of the present invention are useful in flame-retardant materials. The method of testing flame-retardant properties is A.S.T.M. Designation D 2863-70, entitled "Standard Method of Test for Flammability of Plastics Using the Oxygen Index Method."

In the oxygen index (OI) testing procedure the relative flammability of a plastic material such as nylon, or polyethylene terephthalate is determined by measuring the minimum concentration of oxygen in a slowly rising mixture of oxygen and nitrogen that will just support combustion. Consequently the oxygen index expresses such minimum concentration of oxygen, expressed as volume percent, in a mixture of oxygen and nitrogen that will just support combustion.

The test is conducted by burning the material in a test column which is a heat resistant glass tube of 75 mm minimum inside diameter and 450 mm minimum height. At the bottom of the tube is a bed of glass beads about 100 mm deep to mix and distribute the gas mixture. Within the glass tube used as the test column there is a specimen holder to support the treated plastic material while the apparatus is supplied with oxygen and nitrogen flow and control devices. The apparatus is also provided with an igniter which is a separate tube through which a combustible gas such as natural gas is used to ignite the test specimen. In the present testing program glass scrim supported molded sheets of nylon or polyethylene terephthalate ca. 0.2 mm thick and about 25 mm by 100 mm in size are used as the test specimens which are prepared from nylon or polyethylene terephthalate powder and 1% to 20° by weight of the fire retardant additive; the data in the present work correspond to about 10% by weight of additive. As a result of the molding of the organic polymer, e.g, nylon or polyethylene terephthalate, and the additive, an intimate admixture or melt of the molecules of the components is obtained.

In conducting the test, the specimen is clamped in the holder in the test column after which the desired initial concentration of oxygen is introduced to the ignited specimen. A number of tests are conducted to determine the minimum concentration of oxygen that will just support combustion.

The present condensation products are useful in combination with organic polymers generally to reduce combustibility. The normally flammable organic polymers which are rendered fire retardant in accordance with the invention may be natural or synthetic but are preferably a solid synthetic polymer, more preferably a nylon or ester type polymer. Examples of the polymer are cotton, wool, silk, paper, natural rubber, and paint, and also the high molecular weight homopolymers and copolymers of amides, e.g., (nylon 6,6 and nylon 6). Other polymers include esters such as polyethylene terephthalate, and polymers of other unsaturated aliphatic and aromatic hydrocarbons, e.g. ethylene, propylene, butylene, styrene, etc., and also acrylic polymers, e.g., polyacrylonitrile, polymethyl methacrylate, alkyd resins, as well as cellulose derivatives, e.g., cellulose acetate, methyl cellulose, etc. Still other polymers include epoxy resins, furan resins, isocyanate resins such as polyurethanes, melamine resins, vinyl resins such as polyvinyl acetate and polyvinyl chloride, resorcinol resins, synthetic rubbers such as polyisoprene, polybutadiene-acrylonitrile copolymers, butadiene-styrene polymers, butyl rubber, neoprene rubber, ABS resins and mixtures thereof. Since the compositions of the invention are unusually effective flame retardants they are normally combined in flame retarding proportions with the organic polymer at relatively low concentrations, e.g., about 1–20 wt. %, preferably about 3–15% based on additive plus the polymeric substrate, such as by milling, or impregnation, e.g., from a water or alcohol dispersion or solution or by dissolving or dispersing in the molten polymer before extrusion such as in the form of fibers or sheets. It should be noted that it is within the scope of the invention to incorporate such ingredients as dyes, pigments, stabilizers, antioxidants, antistatic agents and the like into the novel compositions.

The following examples illustrate specific embodiments of the invention but are not restrictive of the scope of the invention:

EXAMPLE 1

A stirred mixture of 0.1 mole each of the cyclic hydrogenphosphonate, 5,5-bis(bromomethyl)-2-H-2-oxo-1,3,2-dioxaphosphorinane, having the structure,

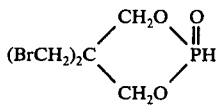

and of phenyl isocyanate in 50 ml. of benzene is treated with 6–8 drops of triethylamine. This causes a temperature increase of about 45° C, and a solid product separates. The mixture is warmed to 80° C, filtered while hot, and the solid product is washed with benzene and dried, giving a white solid, m.p. 167°–169° C, $^{31}$P nmr 10.8 ppm, which is 5,5-bis(bromomethyl)-2-oxo-2-(phenylcarbamoyl)-1,3,2-dioxaphosphorinane, having the structure,

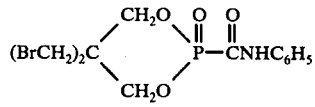

Other basic catalysts which accomplish the same result are N-ethylpiperidine; N,N-dimethylaniline; triethylenediamine; tetrabutylammonium butoxide; and sodium methoxide.

Analogous cyclic phosphorus compounds are obtained when other isocyanates and isothiocyanates are used, specifically p-toluenesulfonylisocyanate, methyl sulfonylisocyanate, ethyl sulfonylisocyanate, phenylsulfonylisocyanate, chlorophenylsulfonyl isocyanate, p-nitrophenylsulfonylisocyanate, p-nitrophenylisocyanate, allyl isocyanate, p-chlorophenylisocyanate, 2-fluorophenylisocyanate, α,α,α-trifluoro-m-tolyl isocyanate, methyl isocyanate, and 3-bromophenylisocyanate. Examples of other isothiocyanates that can be used to prepare analogous cyclic phosphorus compounds are: allylisothiocyanate, ethyl isothiocyanate, 4-fluorophenyl isothiocyanate, naphthyl isothiocyanate, methyl isothiocyanate, and 4-chloro-2-naphthyl isothiocyanate.

EXAMPLE 2

A mixture of 0.1 mole of 3,9-H-3,9-dioxa-2,4,8,10-tetraoxa-3,9-diphosphaspiro[5.5]undecane, having the formula shown below:

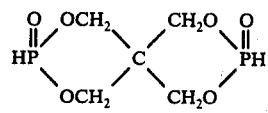

and 0.22 mole of phenyl isocyanate in 100 ml. of benzene is stirred as triethylamine is added dropwise, and the mixture is warmed to reflux. An additional 50 ml. of benzene is added to aid stirring. The temperature is kept at 70° to 80° C for 1 hr, and then the reaction mixture is filtered while hot. The solid product is washed with benzene, water, and acetone, giving a white solid, m.p. 229°–232°, $^{31}$P nmr 8.9 ppm, which is 3,9-dioxo-3,9-bis(-phenylcarbamoyl)-2,4,8,10-tetraoxa-3,9-diphosphaspiro[5.5]undecane,

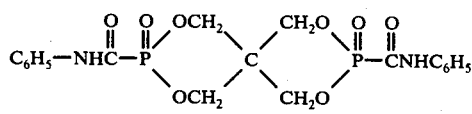

EXAMPLE 3

A mixture of 0.1 mole of 5,5-bis(bromomethyl)-2-H-2-oxo-1,3,2-dioxaphosphorinane, having the structure,

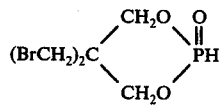

and 0.1 mole of benzylidenemethylamine in 100 g. of benzene is stirred and warmed at 45°–50° C for 1 hr. The reaction mixture is then cooled and filtered. The solid collected is washed with benzene and then dried at 65°/0.15 mm., giving a white solid, m.p. 93.0°–95.5°, $^{31}$P nmr −19.0 ppm, that is 5,5-bis(bromomethyl)-2-[α-(methylamino)benzyl]-2-oxo-1,3,2-dioxaphosphorinane,

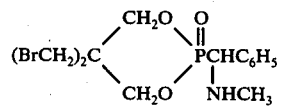

Analysis - Calcd. for $C_{13}H_{18}Br_2NO_3P$: 36.56C; 4.25H; 37.42 Br; 3.28N; 7.25P. Found: 36.46C; 4.24H; 37.42 Br; 3.24N; 7.38P.

EXAMPLE 4

Similarly, the hydrogen phosphonate of Example 2 reacted with benzylidenemethylamine gives a white solid, m.p. 174°–182° C, $^{31}$P nmr −19.6 ppm, which is 3,9-bis[α-(methylamino)-benzyl]-3,9-dioxo-2,4,8-10-tetraoxa-3,9-diphosphaspiro[5.5]undecane,

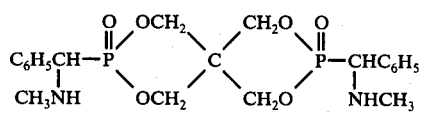

Similar products are obtained when using benzylideneethylamine, p-chlorobenzylidenemethylamine, or methylbenzylidenemethylamine.

EXAMPLE 5

A mixture of 30.8g. of the hydrogenphosphonate used in Example 1 and 19.7 g. of p-toluenesulfonylisocyanate in 100g of benzene is stirred under nitrogen and warmed at 45°–50° C for 1 hr. The reaction mixture is then cooled and filtered. The solid collected is recrystallized from benzonitrile, giving a white solid, m.p. 179°–186°, $^{31}$P nmr 10.3 ppm, which is 5,5-bis(-bromomethyl)-2-(p-toluenesulfonylcarbamoyl)-1,3,2-dioxaphosphorinane,

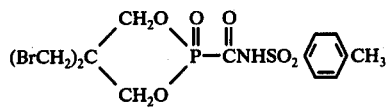

Analogous cyclic phosphorus compounds are obtained when other sulfonyl isocyanates are used in the same reaction, e.g. p-toluenesulfonylisocyanate, methyl sulfonylisocyanate, ethyl sulfonylisocyanate, phenylsulfonylisocyanate, chlorophenylsulfonyl isocyanate, and p-nitrophenylsulfonylisocyanate.

EXAMPLE 6

A mixture of 0.1 mole of the starting hydrogenphosphonate of Example 2 and 0.2 mole of allyl isothiocyanate in 200 ml of dimethylformamide and 20g of triethylamine is stirred and warmed at 65° C for 1 hr. The reaction mixture is then stripped to 80° C at reduced pressure, and the residue is recrystallized from benzene-acetonitrile and from o-dichlorobenzene, giving yellow solid, m.p. 230° (dec.), $^{31}$P nmr 10.2 ppm, which is N,N'-diallyl-3,9-dioxo-2,4,8,10-tetraoxa-3,9-diphosphaspiro[5.5]undecane-3,9-dithiocarboxamide,

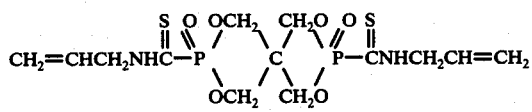

Analysis- Calcd. for $C_{13}H_{20}N_2O_6P_2S_2$: C, 36.62; H, 4.73; N, 6.57; P, 14.53; S, 15.04. Found: C, 36.66 H; 4.73; N, 6.52; P, 14.62; S, 15.15.

Examples of other isothiocyanates that can be used to prepare analogous cyclic phosphorus compounds are: allylisothiocyanate, ethyl isothiocyanate, 4-fluorophenyl isothiocyanate, naphthyl isothiocyanate, methyl isothiocyanate, and 4-chloro-2-naphthyl isothiocyanate.

EXAMPLE 7

Flame retardancy tests are conducted using typical compounds of the invention, specifically the compounds of the above examples. These compounds do not burn readily when subjected to heat and a flame, and they also improve the flame retardant properties of polyamides, specifically nylon-6,6 and of polyethylene terephthalate, at concentrations of 1–20% by weight, preferably 3–15% by weight, based upon the total mixture, obtained by milling, or impregnation or by dissolving or dispersing in the polymer in molten form before extrusion such as in the form of fibers or sheets. It should be noted that it is within the scope of the invention to incorporate such ingredients as dyes, pigments, stabilizers antioxidants, antistatic agents, and the like into the novel compositions.

Test data of the oxygen index test described above for certain compounds at 10% in polyethylene terephthalate are set forth below:

| Compound of Example | O-I Value |
|---|---|
| 1 | 25.7 |
| 2 | 24.5 |
| 3 | 24.5 |
| 4 | 23.5 |

The azomethine, sulfonyl isocyanate, isocyanate, and isothiocyanate, derivatives of the invention, as a group have flame retardant properties for polyethylene terephthalate and also polyamides such as nylon 6,6.

What is claimed is:

1. A cyclic phosphorus compound having the formula

where Y is selected from the group consisting of

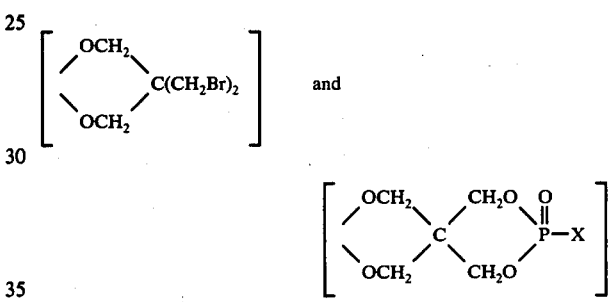

and where X is selected from the group consisting of

| | |
|---|---|
| $-\text{CHNH}(R_b)$<br>$\|$<br>$(R_a)$ | where R is an alkyl radical of 1 to 4 carbon atoms, and $R_b$ is a phenyl radical of 6 to 10 carbon atoms, |
| $\overset{O}{\underset{\|}{-\text{CNHSO}_2(R_c)}}$ | where $R_c$ is phenyl with 0 to 2 halogens, or phenyl with 0 to 2 nitro groups, or phenyl with 0 to 2 methyl groups, |
| $\overset{O}{\underset{\|}{-\text{CNH}(R_d)}}$ | where $R_d$ is phenyl with 0 to 2 halogen atoms, or phenyl with 0 to 2 methyl groups, or an alkyl or alkenyl radical of 1 to 3 carbon atoms, and |
| $\overset{S}{\underset{\|}{-\text{CNH}(R_e)}}$ | where $R_e$ is phenyl with 0 to 2 halogens, or alkyl or alkenyl of 1 to 3 carbon atoms. |

2. Cyclic phosphorus compound as in claim 1 having the formula

where X is the group

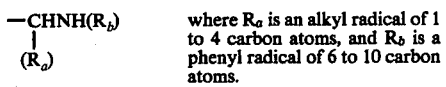

3. Cyclic phosphorus compound as in claim 1 having the formula

where X is the group

where $R_c$ is phenyl with 0 to 2 halogens, or phenyl with 0 to 2 nitro groups, or phenyl with 0 to 2 methyl groups.

4. Cyclic phosphorus compound as in claim 1 having the formula

where X is the group

where $R_d$ is phenyl with 0 to 2 halogen atoms, or phenyl with 0 to 2 methyl groups, or an alkyl or alkenyl radical of 1 to 3 carbon atoms.

5. Cyclic phosphorus compound as in claim 1 having the formula

where X is the group

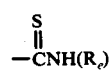
where $R_e$ is phenyl with 0 to 2 halogens, or alkyl or alkenyl of 1 to 3 carbon atoms.

6. The cyclic phosphorus compound

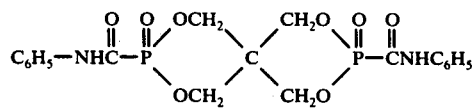

7. The cyclic phosphorus compound

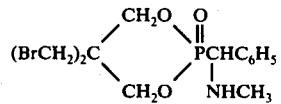

8. The cyclic phosphorus compound

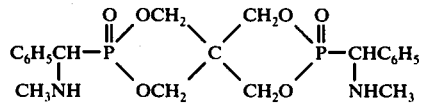

9. The cyclic phosphorus compound

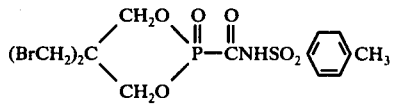

10. The cyclic phosphorus compound

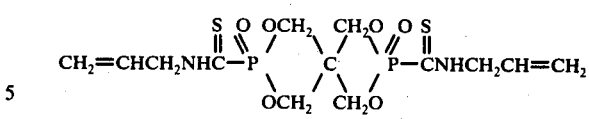

11. The combination of an organic polymer together with a phosphonate adduct having the formula

where Y is selected from the group consisting of

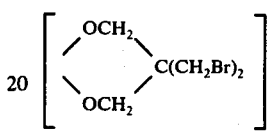 and

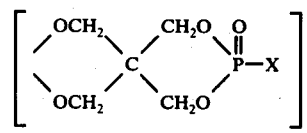

and where X is selected from the group consisting of

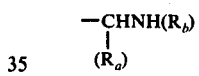 where R is an alkyl radical of 1 to 4 carbon atoms, and $R_b$ is a phenyl radical of 6 to 10 carbon atoms,

 where $R_c$ is phenyl with 0 to 2 halogens, or phenyl with 0 to 2 nitro groups, or phenyl with 0 to 2 methyl groups,

 where $R_d$ is phenyl with 0 to 2 halogen atoms, or phenyl with 0 to 2 methyl groups, or an alkyl or alkenyl radical of 1 to 3 carbon atoms, and

 where $R_e$ is phenyl with 0 to 2 halogens, or alkyl or alkenyl of 1 to 3 carbon atoms.

12. The combination of an organic polymer together with the compound

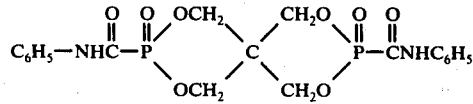

13. The combination of an organic polymer together with the compound

14. The combination of an organic polymer together with the compound

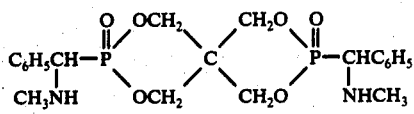

15. The combination of an organic polymer together with the compound

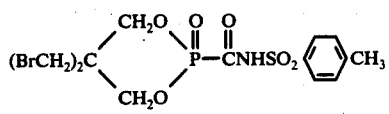

16. The combination of an organic polymer together with the compound

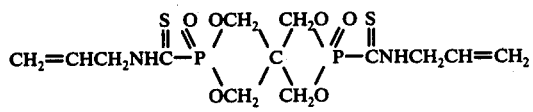

17. Process for preparing a phosphonate adduct which comprises admixing at 0° C to 100° C formic acid with a phosphorohalidite, having the formula

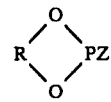

where R is an alkylene, or haloalkylene group of a 1,2-glycol having from 2 to 8 carbon atoms, or of a 1,3-glycol having from 3 to 8 carbon atoms, and Z is Cl or Br, and thereafter treating the resulting intermediate with a member selected from the group consisting of

| | |
|---|---|
| $R_aCH=NR_b$ | where $R_a$ is an alkyl radical of 1 to 4 carbon atoms, and $R_b$ is a phenyl radical of 6 to 10 carbon atoms, |
| $R_cSO_2NCO$ | where $R_c$ is phenyl with 0 to 2 halogens or phenyl with 0 to 2 nitro groups, or phenyl with 0 to 2 methyl groups, |
| $R_dNCO$ | where $R_d$ is phenyl with 0 to 2 halogen atoms, or phenyl with 0 to 2 methyl groups, or an alkyl or alkenyl radical of 1 to 3 carbon atoms, and |
| $R_eNCS$ | where $R_e$ is phenyl with 0 to 2 halogen or alkyl or alkenyl of 1 to 3 carbon atoms, | the said treating being conducted in the presence of a basic catalyst.

* * * * *

UNITED STATES PATENT AND TRADEMARK OFFICE
CERTIFICATE OF CORRECTION

PATENT NO. : 4,073,767
DATED : February 14, 1978
INVENTOR(S) : Gail H. Birum

It is certified that error appears in the above-identified patent and that said Letters Patent are hereby corrected as shown below:

Claim 1, in column 10, line 39, "R" should read $--R_a--$.

Claim 11, in column 12, line 33, "R" should read $--R_a--$.

Signed and Sealed this

Ninth Day of January 1979

[SEAL]

Attest:

RUTH C. MASON
Attesting Officer

DONALD W. BANNER
Commissioner of Patents and Trademarks